United States Patent [19]
Mayled

[11] Patent Number: 5,860,555
[45] Date of Patent: Jan. 19, 1999

[54] STORAGE AND SHIPPING CONTAINER

[76] Inventor: Edward C. Mayled, 28 Groveland Crescent, Brampton, Ontario, Canada, L6S 1L2

[21] Appl. No.: 477,140

[22] Filed: Jun. 7, 1995

[51] Int. Cl.[6] .............................. B65D 5/40; B65D 5/56
[52] U.S. Cl. ..................... 220/403; 220/404; 220/410; 229/131.1; 229/142; 229/148; 229/907
[58] Field of Search ................................ 229/131.1, 142, 229/148, 150, 907; 220/403, 404, 408, 410, 908, 910

[56] References Cited

U.S. PATENT DOCUMENTS

| | | | |
|---|---|---|---|
| 1,247,237 | 11/1917 | Doble | 229/131.1 |
| 1,308,883 | 7/1919 | Weis | 229/131.1 |
| 1,861,206 | 5/1932 | Burgess | 229/150 |
| 2,107,614 | 2/1938 | Kotcher et al. | 229/131.1 |
| 2,343,857 | 3/1944 | Morgenroth | 229/131.1 |
| 4,863,052 | 9/1989 | Lambert | 229/907 |
| 5,074,429 | 12/1991 | Konkeil et al. | 220/410 |
| 5,156,295 | 10/1992 | Gordon et al. | 220/403 |
| 5,356,022 | 10/1994 | Tipps | 229/131.1 |

FOREIGN PATENT DOCUMENTS

| | | | |
|---|---|---|---|
| 2081680 | 2/1982 | United Kingdom | 229/150 |
| 2085409 | 4/1982 | United Kingdom | 229/907 |

*Primary Examiner*—Gary E. Elkins
*Attorney, Agent, or Firm*—Edward H. Oldham

[57] ABSTRACT

A container which is useful in storing articles which are to be recycled until the filled container is returned to the original manufacturer or recycling depot. The container has a port through which cartridges may be conveniently inserted to be stored. The container, which has a plastic bag in communication with the port, is preferably supplied to the consumer as a folded blank and which may be easily erected by the consumer to form a recycling container.

2 Claims, 5 Drawing Sheets

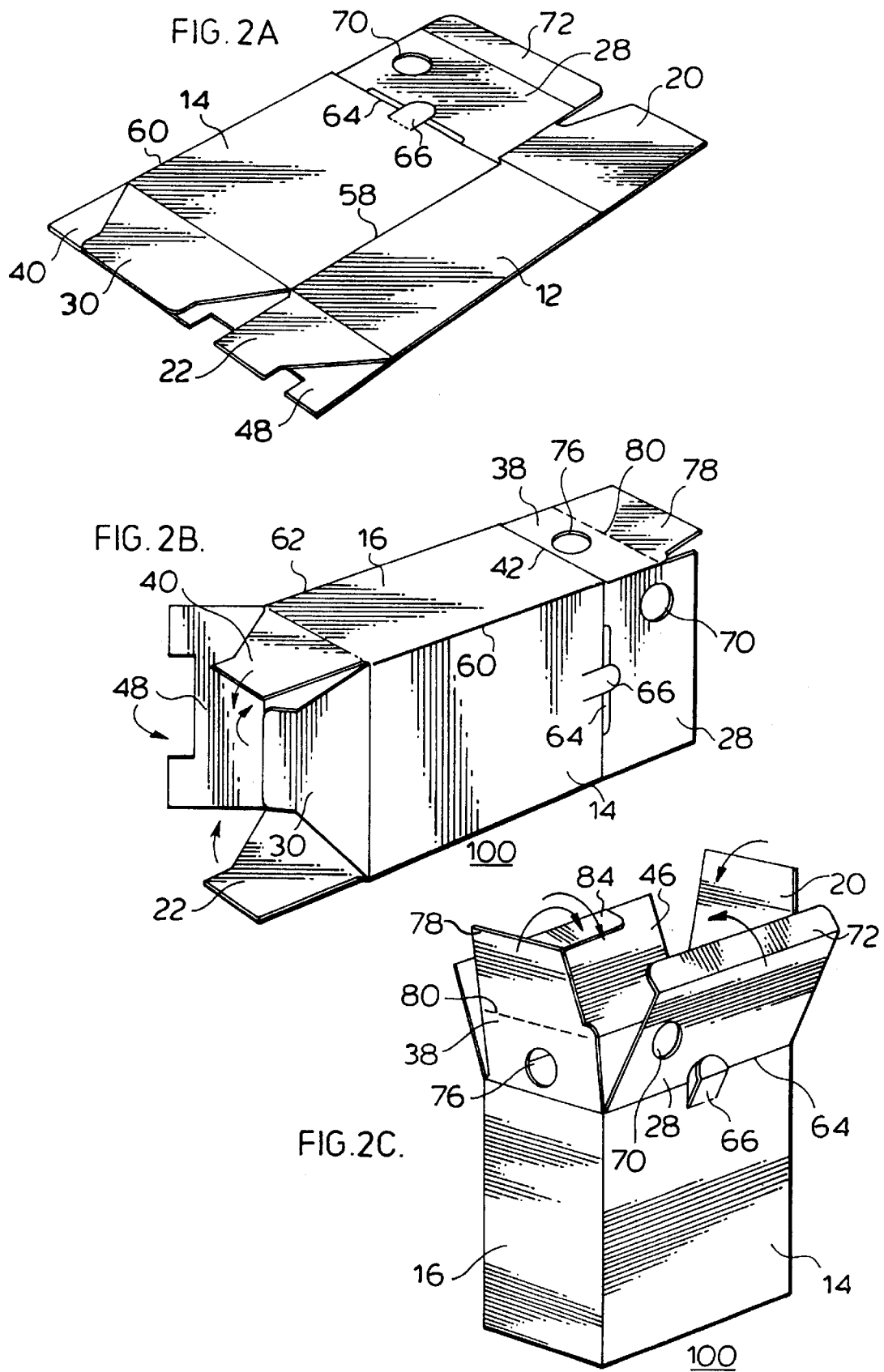

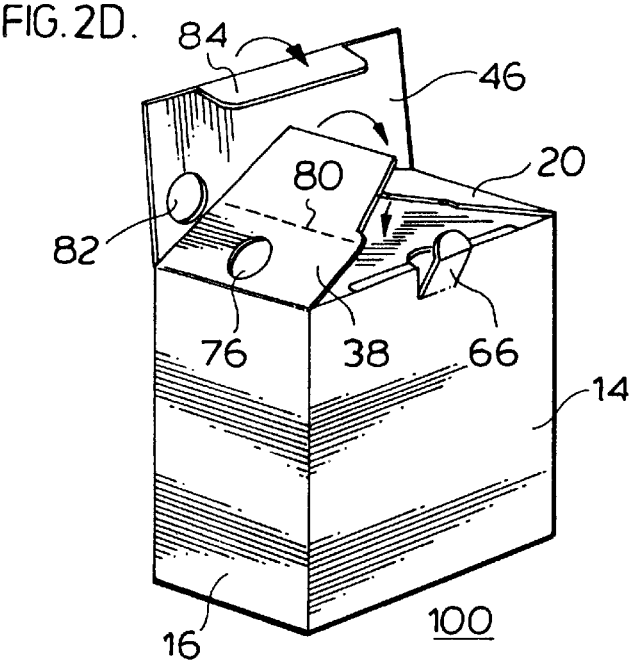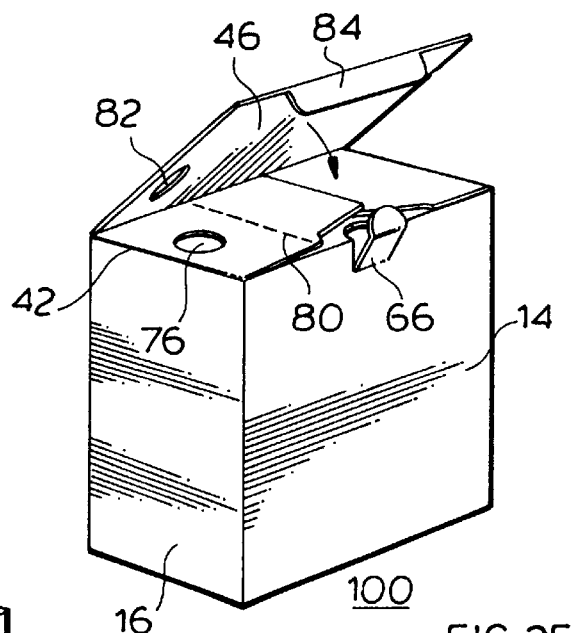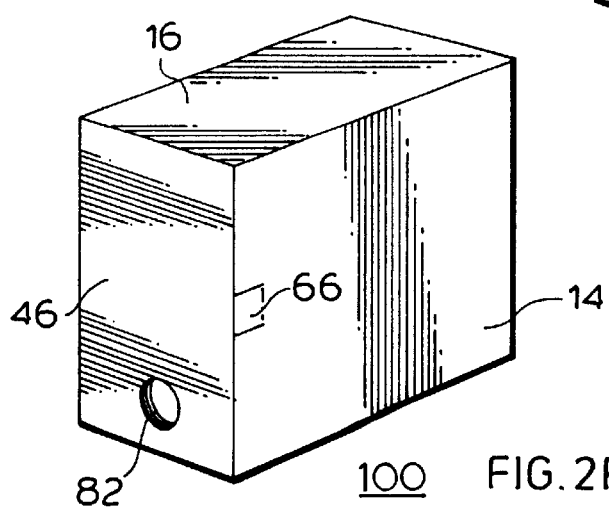

STORAGE AND SHIPPING CONTAINER

BACKGROUND OF THE INVENTION

This invention relates to a container which may be used to collect and store articles which by their nature have a limited useful life. When an article of the type mentioned above has reached the end of its useful life, it may be inserted in the container where it may be conveniently stored until the container is completely filled. The container may also house a plastic bag in its interior, if the exhausted articles are not dry. The container may preferably have a port in one end thereof for insertion of the exhausted articles and the plastic bag may be made to co-operate with the port so that when an article is inserted into the aperture in the container, it will in fact be received in the plastic bag in the interior of the container, thus protecting the container from exposure to any liquids which the exhausted articles might contain.

It is most important that the container as proposed is leakproof because the container and the exhausted containers it contains will be returned to the designated recycling authority through the post office.

Any container leaking its contents (in this instance, water) would suffer immediate rejection by the postal authorities.

DESCRIPTION OF PRIOR ART

This invention is directed to a container to receive specific articles which have a limited useful life, and which must be replaced by the user on a fairly frequent basis. Specifically, this invention is directed to charcoal-type water filters which are used in water filtering devices which may be found in large numbers in the homes of the consuming public.

The specific filter modules with which this invention is concerned are cartridge type filters sold under the trademarks, BRITA, JAMIESON, AQUAPRESSURE and WATER DOCTOR and generally have their origin with the BRITA WASERFILTER GmbH and AQUASELECT of Germany.

Because all these filter cartridges have a standard configuration common to all the above named products, it is possible to provide a standard container which may receive and store such exhausted filter cartridges. The container will help relieve the landfill sites used by municipalities of the burden of storing the large number of expended filter cartridges estimated to be in the order of millions. (Statistics have shown, for instance, that over 10 million filters manufactured and sold by sales representatives of the above companies have found their way into landfill sites in the province of Ontario alone).

The filter cartridges are of a somewhat cylindraceous shape, and are usually composed of a hard plastic material to form the outer shell, which houses the granulated charcoal, which is the active material in the filter, and which, through use, becomes loaded with adsorbed material to the point where the filter cartridge must be replaced.

If some method can be found to reduce the loading on the waste collection and disposal systems, by some alternate collecting device for such expended cartridges, the savings could be very substantial. (Only one company in Canada and the U.S.A. recycles its carbon filter material at the present time.)

When the recycling container is filled with expended filter cartridges, it may be returned to the manufacturer or other recycling agency so that the expended cartridges may be recycled.

SUMMARY OF THE INVENTION

It is an object of this invention to provide a simple container, which may be shipped in a flattened state and which may be assembled by an unskilled person into a fairly permanent container which may receive a predetermined number of expended cartridges in its filled state.

A plastic bag is previously secured to the aperture of the container by means of hot glue spotted around the aperture on the panel containing the aperture of the container. The erection of the container does not require any extraordinary dexterity on the part of the consumer to assemble the container and its attached plastic bag. The consumer is only required to ensure that the plastic bag is inside the assembled container when the assembly of the container is underway and also when the operation is completed.

The plastic bag which effectively functions as a liner inside the container provides assurance that the container will not be subjected to ingress of liquid from any of the filter cartridges inserted into the container which by their nature may contain water in varying amounts at the time of insertion into the container. It has been found that most consumers do not take the time to dry the spent filters before insertion into the container.

When the container is filled to capacity with expended cartridges, the plastic bag which is attached to the container at the container port, is pulled away from its position occupied during the time the container was being filled, and relocated to effectively seal the bag in the container so that the contents of the bag will not be spilled during the return voyage to the recycling depot. No twist ties, tapes or strings are required to seal the bag in the container.

When the plastic bag is effectively sealed, the box shaped container may be completely closed by closing the flaps in the side bearing the port to prevent tampering with the plastic bag or the contents contained therein.

It is expected that the container and its contents will be returned to the recycling authority by the post office.

When the container reaches its ultimate destination such as a recycling depot, or a remanufacturing operation, the container may be opened to remove the plastic bag and its contents without spilling the contents of the bag during the opening operation.

The package may be used to conveniently house articles for recycling which are by their nature dry, and in this instance, no plastic bag type liner will be employed i.e. prescription vials, photo film outer vials, disposable cameras, etc.).

BRIEF DESCRIPTION OF THE DRAWINGS

Figure 1:
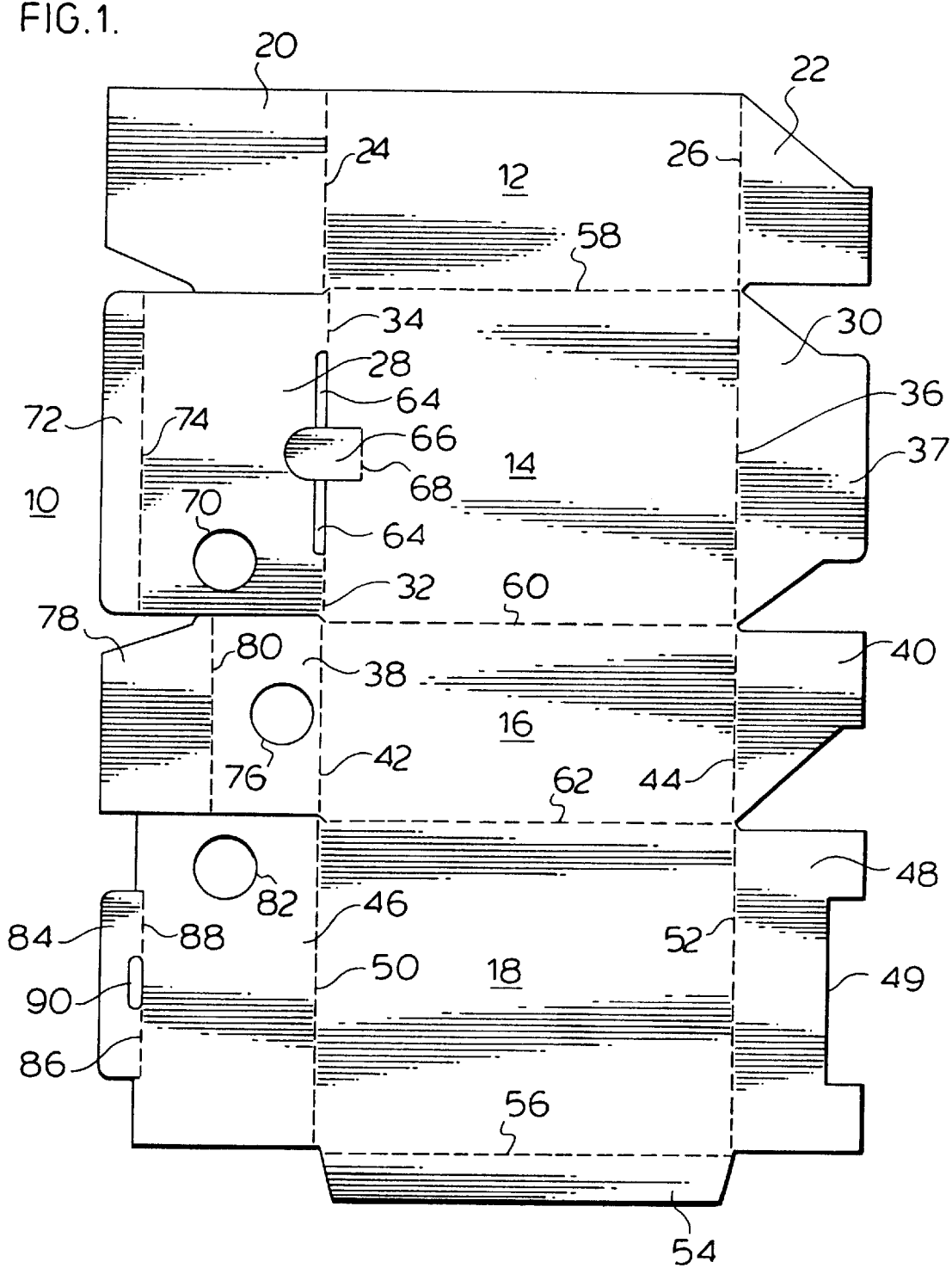

Having thus described the nature of the invention, reference will now be made to the accompanying drawings showing by way of illustration a preferred embodiment thereof, and in which:

FIG. 1 is a drawing of the blank used as the outer container for this invention.

FIGS. 2A through 2F show the assembly operation of the container of this invention.

Figure 3:
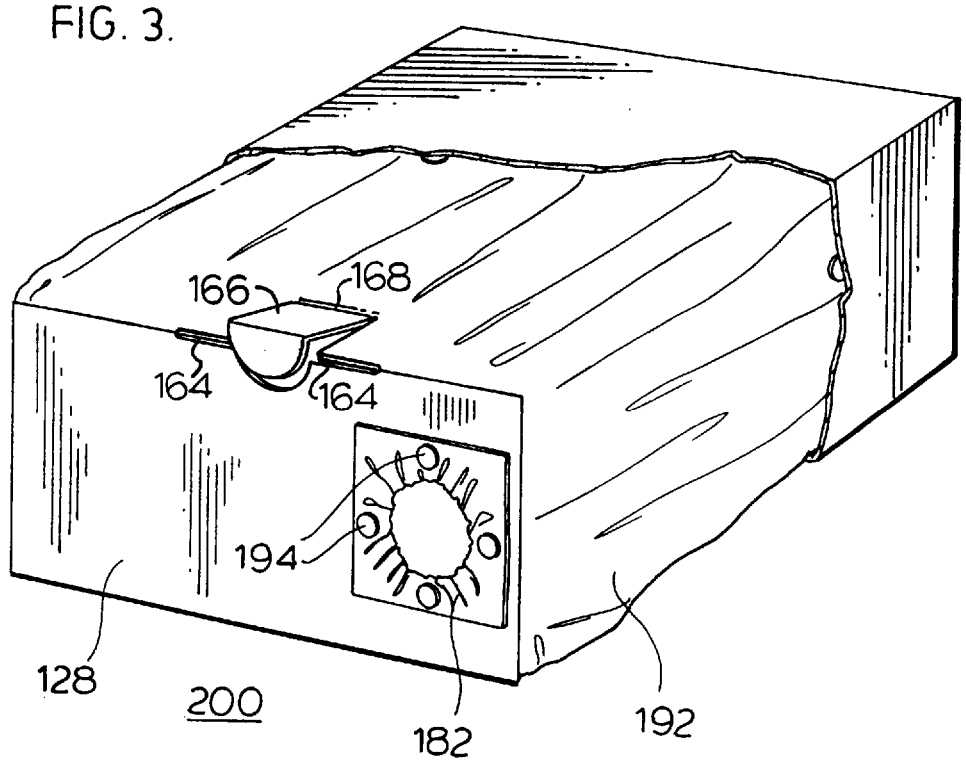

FIG. 3 is an enlarged view of the interface of the plastic bag and the recycling container.

FIG. 4A through 4E show the steps necessary to prepare the recycling container for shipment.

DESCRIPTION OF THE PREFERRED EMBODIMENT

Referring to FIG. 1, a carton blank 10 is shown which will ultimately be folded into a container which forms part of this invention.

Carton 10 is shown having four wall panels 12, 14, 16, 18 and each panel has a pair of depending flaps extending therefrom. For instance, panel 12 has a pair of flaps 20 and 22 extending therefrom, the flaps being divided from the panel 12 by means of scorelines 24 and 26.

Similarly, panel 14 is shown having flaps 28 and 30 extending therefrom, with scorelines 32, 34 and 36 forming the boundaries between flaps 28 and 30 and panel 14.

In the same manner, panel 16 is shown having flaps 38 and 40 extending therefrom and the division in this instance being made by scorelines 42 and 44.

Panel 18 is shown having flaps 46 and 48 extending therefrom such that the division of the panel 18 and flaps 46 and 48 is made by scorelines 50 and 52. Panel 18 has a seal flap 54 extending therefrom wherein score line 56 forms the division between the seal flap 54 and panel 18.

In addition, panels 12, 14, 16 and 18 are divided by scorelines 58, 60 and 62.

Flap 28 is shown attached to panel 14 at the scorelines 32 and 34, but a slot 64 is cut in the score line to intersect the scorelines 32 and 34. A folding tab 66 is shown extending from the score line 68 in panel 14.

Flap 28 contains an aperture 70 hereinafter referred to as the primary aperture in carton 10, and flap 10 has a second flap 72 extending therefrom which is formed by score line 74.

Flap 38 also has an aperture 76 provided therein and flap 38 has a secondary flap 78 extending therefrom, this flap being formed by a scoreline 80.

Panel 46 also has an aperture 82 provided therein which is of slightly less diameter than apertures 70 and 76 in panels 28 and 38 respectively. Panel 46 also has a secondary flap 84 extending therefrom which is divided from the flap 46 by scorelines 86 and 88. A slot 90 is also found joining scorelines 84 and 86.

If the container which is ultimately formed from blank 10 is to be used to store and ship used articles which by their nature are dry, the assembly is quite straight forward.

FIGS. 2A through 2F shows the assembly operation of the container formed from blank 10.

Blank 10 is joined together in the form shown in FIG. 2A. Panel 18 is jointed to panel 12 by gluing the flap 54 to the panel 12 at the edge thereof. It is proposed to use hot glue or some other appropriate method of joining the two panels, the method of joining panels 18 and 12 forms no part of this invention.

The container 100 shown in FIG. 2F is assembled as follows:

The blank 10 is opened as shown in FIG. 2B and the end remote the apertures is assembled as shown. First flap 48 is closed, followed by flaps 22 and 40. Flap 30 is closed in flap 48 by locking the extending tongue 37 into recess 49 of flap 48.

The other end of the container 100 is assembled as shown in FIGS. 2C, 2D and 2E.

First flap 28 is closed with extension flap 72 folded inside panel 18. Next panel 78 is closed followed by panel 20. The closure is now completed by folding panel 46 over the three other panels, so that flap 84 may be inserted in slot 64. When this is accomplished locking member 66 may be inserted in slot 90. This assures the stability of the end closure which now has an aperture leading to the interior of container 100. Aperture 82 is slightly smaller than either of apertures 70 and 76 (which are of about the same size). The container 100 may be modified to accept a plastic bag at the place where the aperture is located.

Figure 4A:
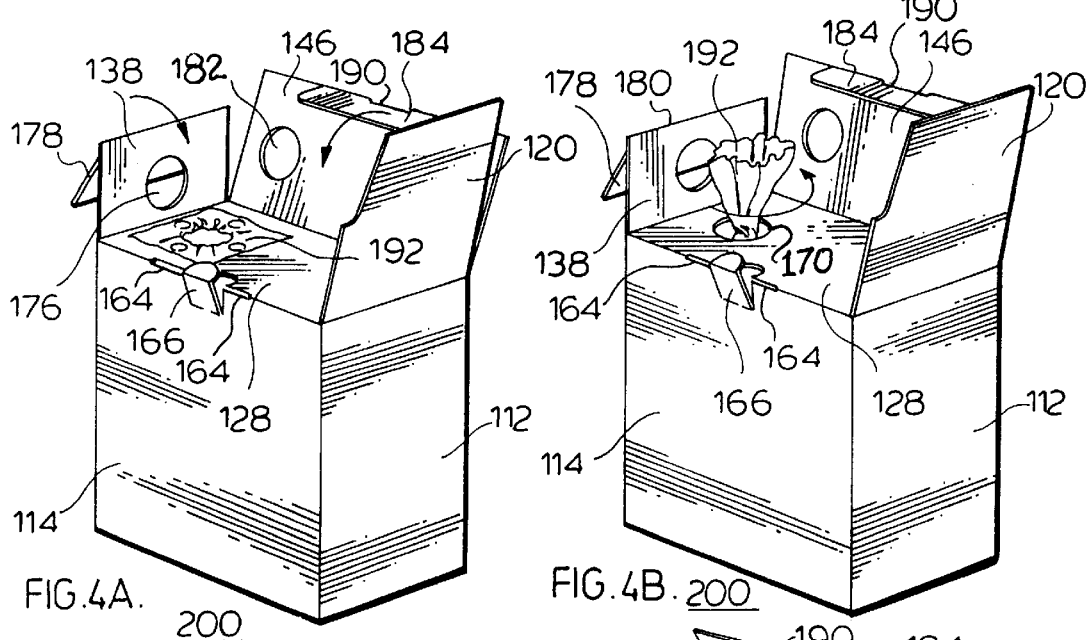

FIG. 4A shows the location of the attachment of the plastic bag to the container 200. Flap 146 corresponds to flap 46 on container 100 previously. Flap 146 has a secondary flap 184 attached to flap 146 at scorelines 186 and 188 respectively. Slot 190 intercepts the scorelines 186 and 188.

A plastic bag 192 which has the general shape of container 200 (same shape as container 100) and is made to have a neck which is passed through aperture 170 and is held in place by hot glue spots 194.

In this instance the container 200 is identical with container 100 except that flap 128 is now fitted with a plastic bag attached at aperture 170 and the bag 192 has the general shape of the container 200 when assembled.

The box 200 is shipped to the customer in a flattened shipping condition and is assembled in exactly the same sequence as box 100. Care must be taken that the plastic bag 192 is not caught in any of the folds of the container.

When complete, container 200 is identical to container 100 with the exception that a plastic bag may be seen beyond aperture 182 on the inside of container 200.

Basically container 200 is assembled as previously, with the end of the container opposite the end having the cartridge receiving apertures being assembled in exactly the same manner as previously. FIG. 4A shows the routine for closing flaps 124, 128, 142 and 146.

Flap 128 with flap 172 folded over at 90° is closed first, and care must be taken to assure that bag 192 is tucked into the container 200 before the flap 128 is closed. When flap 128 is in the closed position bag 192 will be exposed as it passes through aperture 170 and is glued to flap 128 by hot glue spots 194 (in this instance, four hot glue spots are utilized to hold the, plastic bag in place).

Flaps 120 and 138 are closed next, and the outside flap 146 is closed with flap 184 being inserted in slot 164. Lock 166 secures flap 146 in its closed position as previously in FIGS. 2A through 2F.

The container 200 now may be used to accept spent cartridges until it is filled. At this time the carton must be prepared for shipping to the recycling depot.

Figure 4B:
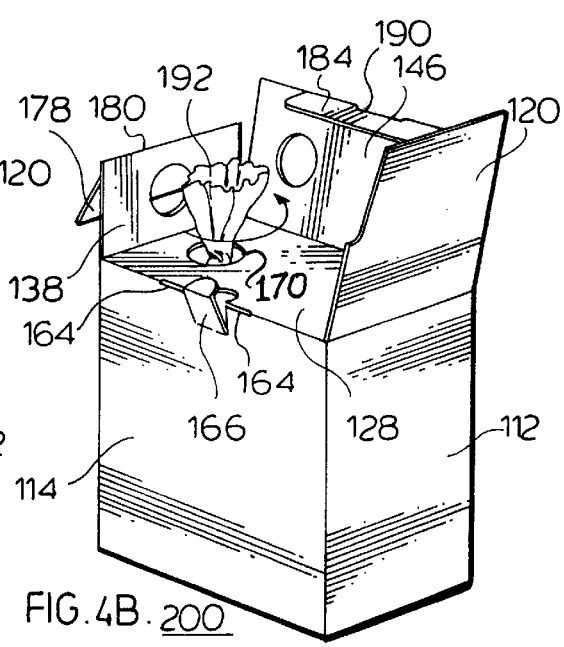

The container 200 is prepared for shipping in accordance with illustrations in FIGS. 4A through FIGS. 4E. Referring to FIG. 4A flap 146 is first opened as are the end flaps 120 and 138 exposing flap 128 to which the neck of bag 192 is attached. The neck of bag 192 is now pulled away from the surface of the flap 128 as shown in FIG. 4B by tearing the glue spots from the surface of the flap 128. The bag will then be released form the surface of flap 128 and the surface where the bag 192 was previously attached now is intact with the exception of some surface spot removal where the hot glue spots were located.

Figure 4C:
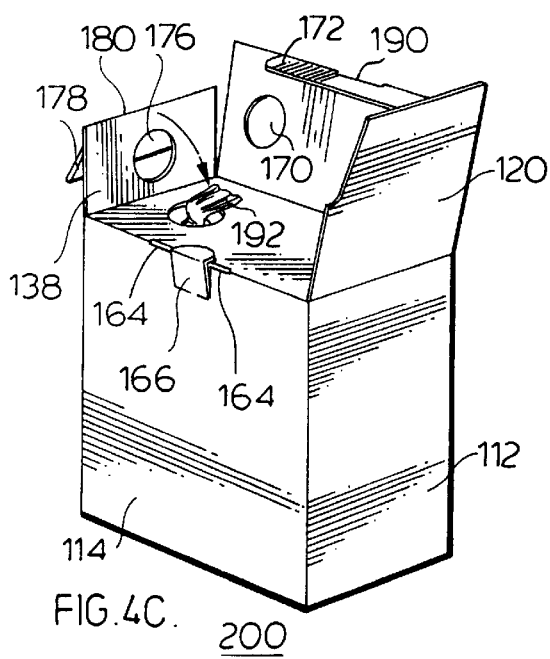
Figure 4D:
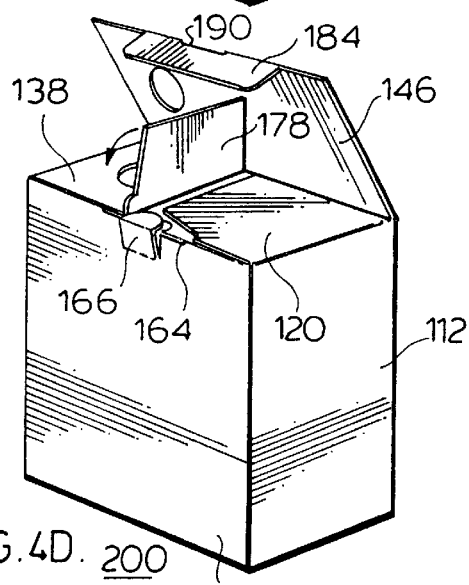
Figure 4E:
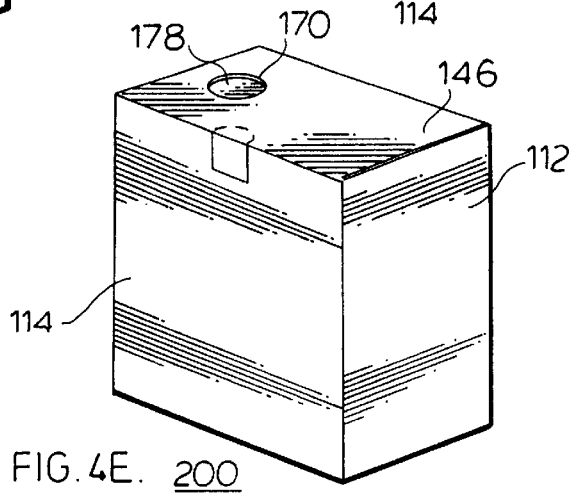

The neck of bag 192 is now twisted tightly and when twisted, the twisted neck is tucked into the crevice formed by flap 128 and panel 118 at the rear of container 200 as shown in FIG. 4C.

Flap 178 has been folded back along the score line 180 so that aperture 176 is now covered and flaps 138 and 120 may now be folded to their closed position, and with flap 178 still covering aperture 176, flap 146 is closed with flap 184 being inserted into slot 164 and flap 166 is inserted into locking slot 190 to secure the lid 146 in place. Tab 166 may be taped shut to increase the security of the package.

Because of the particular configuration used to construct container 200, and the method of fastening the plastic bag to flap 128, the container itself may be recycled and reused by the consumer.

This is made possible by the particular construction of the container which utilizes no glue to hold the flaps 22, 30, 40 and 48 together. Similarly, the flaps 20, 28, 38 and 46 are assembled together without the requirement of any glue as well.

Because the plastic bag is fixed to the flap 128 by means of a minimum number of hot glue spots (hot glue gun) the top surface of flap 128 is not destroyed when the consumer removes the plastic bag from flap 128 in preparation for shipping back to the recycling authority.

The recycling authority opens the container 200 upon receipt and removes the plastic bag and its contents from the container.

A new plastic bag is inserted into aperture 176 and again the new plastic bag is fixed to the flap 128 by means of hot glue spots (preferably 4) to the top surface of flap 128.

The method of fastening the plastic bag to the flap 128 is somewhat unique; in the past, a heat seal coating would have been applied to the surface of the flap 128 and to the mating surface of the plastic bag during the manufacture of both articles. A suitable heating device which would heat the plastic bag and the mating surface of flap 128 would activate the heat seal coating previously applied to both surfaces to cause the surfaces to adhere when the surfaces were pressed together upon heating.

This method of joining the bag to flap 128 has the advantage of providing a large surface adherence but at the time of return of the container 200 to the recycling authority, the surface of flap 128 around the aperture 176 may be destroyed when the consumer pulls the top of the plastic bag away from flap 128 in order to seal the contents of the plastic bag.

When the recycling authority has re-attached the new plastic bag to the flap 128, the container is folded into its flattened configuration in preparation for shipping to the depot where the consumer may pick up the container for future use.

I claim:

1. A shipping and storage container for spent cylindraceous cartridges comprising
   a pair of sidewalls
   a pair of endwalls
   a top wall
   a bottom wall
   wherein the top wall is formed by four co-operating flaps, three of said four co-operating flaps each being provided with apertures, a first pair of said four co-operating flaps extending from said side walls and a second pair of said four co-operating flaps extending from said end walls,
   a first flap of said first pair having an aperture of a predetermined size formed therein, said first flap of said first pair being folded closed first so that it becomes part of the topwall of the container,
   a first flap of said second pair closing over the first flap of said first pair so as to partially overlap said first flap of said first pair in such a manner that the aperture in said first flap of said first pair remains uncovered,
   a second flap of said second pair being folded over said first flap of said first pair so that said apertures in said first flap of said first pair and in the second flap of said second pair are in registry,
   a second flap of said first pair being folded over said previously folded flaps so that all three apertures of the flaps forming the assembled topwall are in registry, to form a port in said topwall of said container,
   said second flap of said first pair being locked into said container to prevent inadvertent opening of said container,
   and wherein said second flap of said second pair is of sufficient length to permit said second flap of said second pair to be folded back upon itself to cover the aperture contained in said second flap of said second pair.

2. A container as claimed in claim 1 in which a plastic bag of a suitable size is fitted to the inside of said container said bag having a neck of such size as to pass through the aperture in said first flap of said first pair, and is attached to an outside surface of said first flap of said first pair so as to communicate with the port in said topwall so as to receive spent water filter cartridges inserted in said port,
   said bag having sealing means to close said bag when said container is to be shipped.

* * * * *